United States Patent
Janssen et al.

(10) Patent No.: US 7,340,082 B2
(45) Date of Patent: Mar. 4, 2008

(54) METHOD AND MEDICAL IMAGING APPARATUS FOR DETERMINING A SLICE IN AN EXAMINATION VOLUME FOR DATA ACQUISITION IN THE SLICE

(75) Inventors: Isabelle Janssen, Erlangen (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 499 days.

(21) Appl. No.: 11/040,971

(22) Filed: Jan. 21, 2005

(65) Prior Publication Data
US 2005/0203372 A1    Sep. 15, 2005

(30) Foreign Application Priority Data
Jan. 22, 2004 (DE) .................... 10 2004 003 381

(51) Int. Cl.
*G06K 9/00* (2006.01)
(52) U.S. Cl. .............. 382/128; 378/8; 378/20; 378/901
(58) Field of Classification Search ........ 382/128, 382/129, 130, 131, 132, 133, 134, 154, 173; 378/4, 8, 20, 21, 23, 27, 901; 600/407, 410, 600/425, 437, 509
See application file for complete search history.

(56) References Cited

U.S. PATENT DOCUMENTS

| | | | |
|---|---|---|---|
| 6,195,409 B1 * | 2/2001 | Chang et al. ............ | 378/20 |
| 6,882,149 B2 * | 4/2005 | Nitz ....................... | 324/309 |
| 2002/0034323 A1 | 3/2002 | Kuth | |
| 2003/0139659 A1 | 7/2003 | Dale et al. | |
| 2003/0199748 A1 | 10/2003 | Camus et al. | |

FOREIGN PATENT DOCUMENTS

| | | |
|---|---|---|
| DE | OS 44 36 263 | 4/1996 |
| DE | OS 197 26 226 | 12/1998 |
| DE | OS 199 20 300 | 11/2000 |
| WO | WO 98/38908 | 9/1998 |
| WO | WO 02/37407 | 5/2002 |

* cited by examiner

*Primary Examiner*—Samir Ahmed
*Assistant Examiner*—Abolfazl Tabatabai
(74) *Attorney, Agent, or Firm*—Schiff Hardin LLP

(57) ABSTRACT

In a method and medical examination apparatus for determination of the position of at least one slice in an examination area in which slice a slice image acquisition of the examination area by means of the examination device is to occur, a 3D image dataset of the examination area is acquired, which is then brought into registration with a chronologically earlier acquired 3D reference image dataset. The slice in the 3D image dataset is determined by at least one reference slice defined in the 3D reference image dataset.

13 Claims, 3 Drawing Sheets

METHOD AND MEDICAL IMAGING APPARATUS FOR DETERMINING A SLICE IN AN EXAMINATION VOLUME FOR DATA ACQUISITION IN THE SLICE

BACKGROUND OF THE INVENTION

1. Field of the Invention

The present invention concerns a method for determining the position of at least one slice in an examining region, in which slice a slice image acquisition of the examining region by means of an imaging device should occur.

2. Description of the Prior Art

The treatment of a pathology in an examining region often demands the timely staggered acquisition of images from the examining region to be able to conduct an check of the treatment or therapy whether the treatment is successful. An example is the treatment of pathologies in the region of the brain, tumors for instance. In the treatment of such a tumor it is naturally important for the doctor to know whether and how the tumor, dependent on the treatment, changes. For this purpose, images defined for the treatment control slice are acquired by magnetic resonance or computed tomography and are evaluated by the doctor. In order to make an informed decision about the success of the treatment, it is naturally important to conduct the image acquisition in a reproducible manner always in the same slice, because only then can a genuine comparison be made between two images acquired successively at intervals of one or more days, weeks or months.

For reproducible slice alignment it is known from U.S. Pat. No. 2003/0139659, to use an atlas containing a multiplicity of comparison images in the form of separate image datasets of real brains, that respectively define specific slices that are relevant and significant.

In operation the examining device, such as a magnetic resonance device, a first set of data of the examining region is acquired, that then can be compared with the information out of the atlas, in which one or more relevant slices have been defined by the user. These slices are then searched by a comparison of the gray scale value distribution of the defined slices and of the acquired examining region in the examining region, and those slices are ascertained having gray scale value distribution features exhibiting a maximum concurrence with the defined slice in the atlas. This principle is naturally applicable as well for the examination of other regions of the body.

Slice determination with one such atlas, however, is not possible if the examining region, as for example the brain, exhibits greater deviations from the normal images in the atlas. This is for instance the case in children, whose brains are undergoing a relatively fast development. The same is true for patients with, for example relatively large tumors. While in adults the anatomy of the brain is overall nearly very similar, and thus the gray scale value distribution as well, is nearly the same in almost all adults, this is not the case in the aforementioned persons due to the clearly different anatomy.

SUMMARY OF THE INVENTION

An object of the present invention is to provide a method and a medical examination apparatus that allow a meaningful comparison to be made of images of arbitrary anatomical regions of a patient respectively obtained at different (offset) points in time that are separated from each other by a time duration that precludes the patient from being positioned in exactly the same positions when data for the respective images are acquired.

This object is achieved in accordance with the invention by a method of the initially described type wherein a 3D image dataset of the examining area is acquired, which is them registered with an earlier acquired 3D reference image dataset, whereupon the slice in the 3D image dataset is ascertained with at least one defined reference slice in the reference image dataset.

The basis of the invention is the creation of a personal-individual reference that is in the form of a three-dimensional reference image dataset of the examining region, such as the head. This is acquired, such as at the outset of a longer time period of treatment, within which multiple control exposures are taken over the treatment course, for instance acquired by magnetic resonance or computed tomography.

In the reference dataset the doctor defines, for example, one or several reference slices, that the doctor wishes to acquire again in later examinations for comparison and control purposes, and in which exactly the later slice image exposures must be acquired anew in order to conduct a true comparison between those circumstances depicted in the images, that must be depicted exactly in the same region.

After such a reference is created, then within the framework of every subsequent examination a three dimensional image dataset of the examining area is acquired, which in a first step is registered with the 3D reference image dataset, i.e. it is subjected to a test, as to how both datasets are positioned relative to one another in the coordinate system of the examining devices. Generally the patient is never positioned exactly the same from scan-to-scan, therefore it is important to determine how both sets of data can be mapped to one another. After the registration has occurred one or multiple slices in the 3D image dataset is/are ascertained on the basis of one or several defined reference slices in the three-dimensional reference image dataset. In this way it is possible, based on the personal-individual image reference, to determine exactly the slice(s) for the follow-up acquisition, that have been defined earlier as reference slice(s) by the doctor.

The inventive method permits an exact slice determination in any patient independently of whether the patient represents a comparison norm.

The ascertainment of one or multiple slices in the 3D image dataset is accomplished on the basis of the gray scale value distribution in the reference slice, by determining the slice that exhibits the maximum gray scale value distribution concurrence. The image data are evaluated using a suitable algorithm, to analyze and find the gray scale value distribution, alternatively the appropriate histogram and any slice or multiple slices, which exhibits the greatest concurrence with the gray scale value distribution of the known, defined reference slice. Due to the situational registration of both datasets, the slice corresponding to the respective reference slice can be ascertained in this way precisely and reliably in the directly acquired three-dimensional image dataset.

The registration of both three dimensional datasets can take place as well with the gray scale value distribution of one or more registration slices or registrations volumes defined in the 3D reference dataset. Here, as well, a suitable algorithm is employed, which acquires and analyzes and searches for the gray scale value distribution in one or multiple registration slices defined in the three dimensional reference image dataset or in the corresponding registration volumes in the three dimensional image dataset, corresponding to the slice(s) or the volume or the volumes that exhibit the maximum concurrence with the distribution of the corresponding registrations slice or volumes.

Should a treatable pathology be located in a reference slice or the registration slice or the registrations volume, this may be partially very drastically changed dependent on the treatment. Associated therewith is unavoidably a noticeable change, that progresses with time, of the gray scale value distribution within the region, and within the reference slice corresponding to that region. The same is true in the case of registration. Locating the change by means of the gray scale value distribution in such a case would not be possible. For this purpose, the invention makes use of segmentation, i.e. one or multiple regions can be defined in the reference image dataset the within the framework of the gray scale value analysis and gray scale value comparison, that should remain unchanged. It is also possible, for example, to define and "cut out" the region of the pathology, so that simply the remaining region, that also by a change of the form or size of the pathology stays unchanged, within the framework of the analysis and the comparisons. Alternatively it is possible to create the segmentation of one or multiple regions, which are considered exclusively within the framework of the comparison and the analysis. That is, the doctor chooses one or multiple regions within the reference slice or volumes that stay unchanged, as well, and can be found again in a later acquired image dataset upon a change of the pathology.

Alternatively, additionally it is possible to undertake the determination of the slice or the registration with at least one anatomical structure defined in a 3D reference image dataset. One such structure is, for instance, the skull bone defined by the gradient. This anatomical marker or markers is/are for registration.

After the determination of the slice, the exposure parameters, needed for the acquisition of the slice image in the determined slice are automatically ascertained and preset by the examination device. At the end of the procedure the examination device is automatically set for image acquisition.

The invention also concerns a medical examination device, designed for the execution of the above-described method.

DESCRIPTION OF THE PREFERRED EMBODIMENTS

Figure 1:
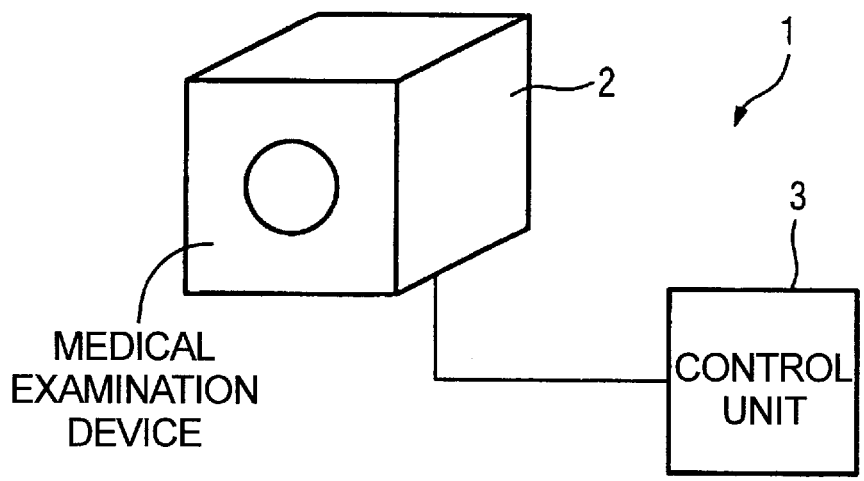
FIG. 1 is a block diagram of the basic components of an examination device in the form of a magnetic resonance device corresponding to the invention.
Figure 2:
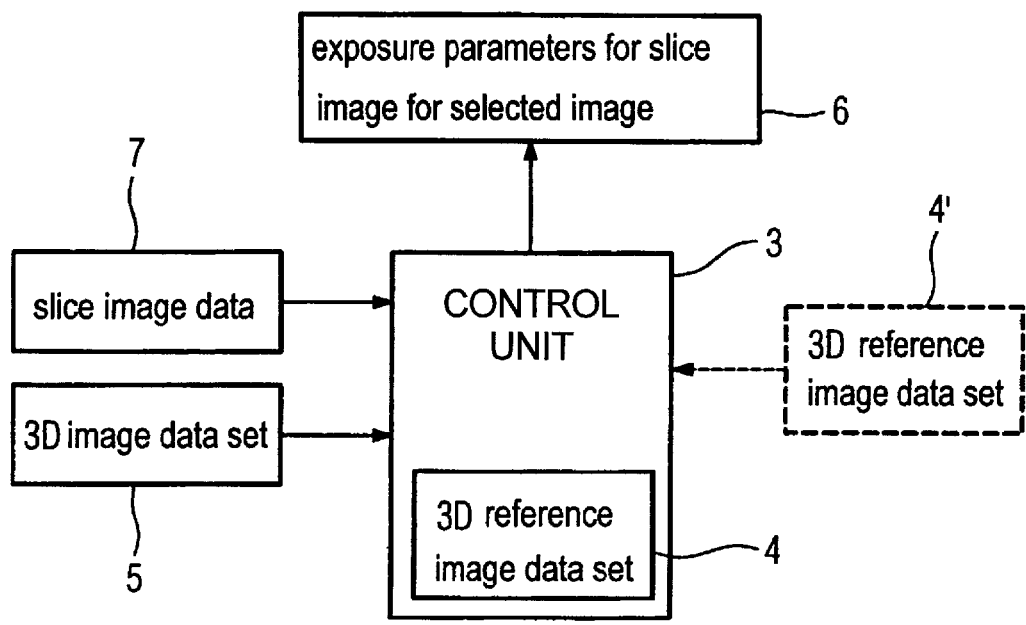
FIG. 2 illustrates the data received from the control unit of the examination device according to FIG. 1.

FIG. 1 shows the basic components of an examination device 1 in the form of a magnetic resonance device 2 corresponding to the invention, the control unit 3 of which is shown enlarged. FIG. 2 explains the operation of the entire device 2, such for as image acquisition and processing controlled by the control unit 3. It is known to obtain slice image exposures of an examination object with the magnetic resonance device 2 . In accordance with the invention a 3D reference image dataset 4 exists in the control unit 3 for the execution of time staggered (offset) slice image exposures of an object with reproducible depiction of a certain slice. This dataset 4 is acquired for instance at the beginning of treatment of the examination region, for example of a tumor in the brain. The 3D reference image dataset 4 can be acquired with the magnetic resonance device 2, or it can be obtained by another examination module of the same or other type and loaded into the control unit 3.

The reference image dataset represents a person's individual situational reference, that describes the condition of the patient or the examination area, that exists as a three dimensional reconstructable volume in the 3D reference image dataset at the point in time of the scan. In this 3D reference image dataset is/are one or multiple reference slice(s) defined by prior observation by a doctor, that show the corresponding regions of the examination region, that are relevant and significant for the diagnosis and monitoring, for example in the treatment of a tumor.

For making a current slice determination in the planning of process control parameters for a current (next) scan, a further updated 3D reference image dataset 5 is obtained and loaded into the control unit 3, after the patient is positioned again in the magnetic resonance device 2 after a lapse of time (for instance, days or weeks) for the approximate determination. A registration instruction is created between both 3D datasets that relates the images to each other, since coordinate systems with respect to one another are known, It is not possible for the patient to be brought into the same exact position in the two subsequent examinations. Consequently both image datasets display the same examination area, but with a somewhat different positioning of the patient. As a result of the registration a display instruction is produced that makes it possible to map every voxel of the 3D image dataset onto a corresponding voxel of the other 3D image dataset, and thus the image can be displayed superimposed, if desired.

Once the registration has taken place, the respective slice and its position in the current 3D image dataset is determined by means of the gray scale value distribution within one or multiple reference slices. This occurs by an analysis of the respective gray scale value distributions, as follows. As soon as the position(s) of one or multiple slices (in which subsequently the data acquisition is to occur to produce slice images that exist in the same slice, or to display the same slice as the reference slice) is/are determined, the control unit 3 determines appropriate scan parameters 6 for the device 2 for that slice image or for subsequent slice images. Subsequently the slice images 7 are acquired and the corresponding slice image data are loaded into the control unit 3, which then evaluates the data and produces corresponding two dimensional slice images for display on a monitor for diagnosis and assessment by the doctor.

Figure 3:
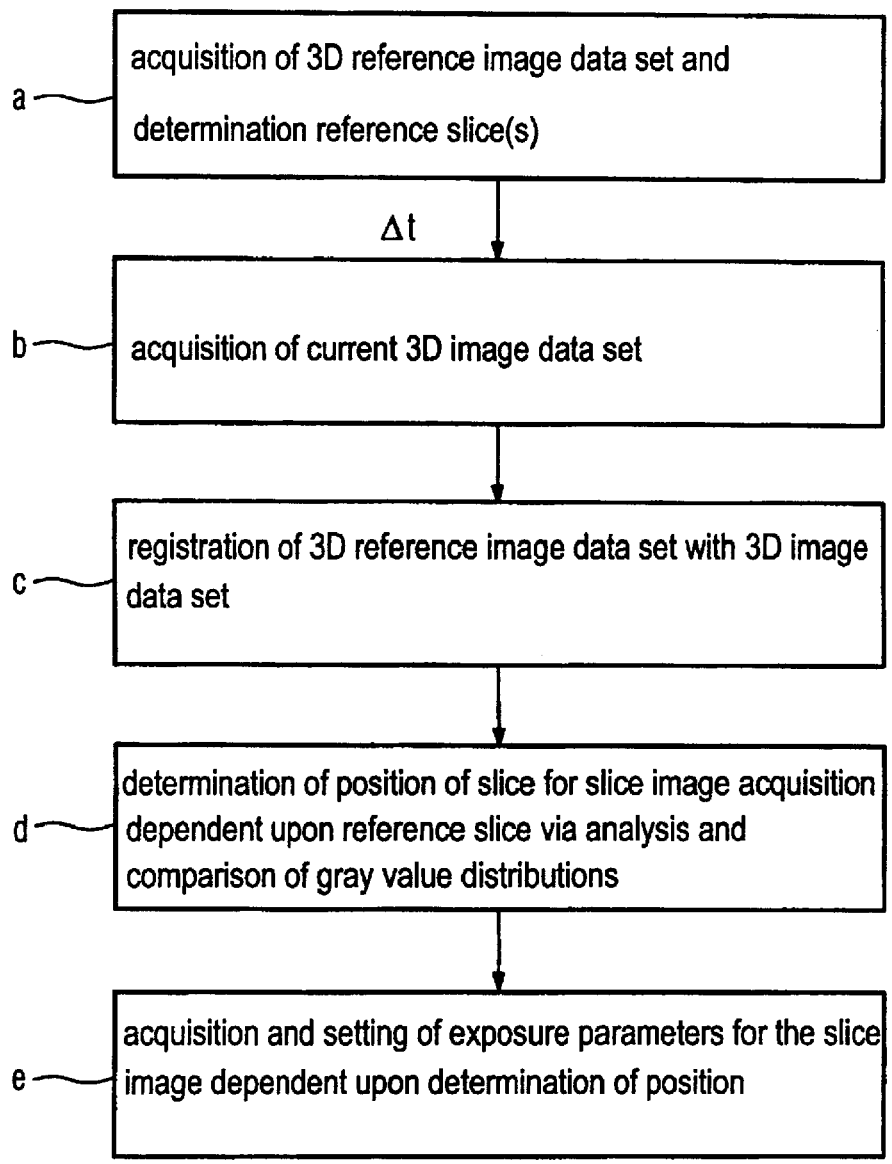
FIG. 3 is a flowchart of the basic steps of the slice determination method according to the invention.

FIG. 3 depicts the basic procedure of the slice determination method according to the invention in the form of a flowchart. Initially in step a the reference image dataset is acquired as described above. After the acquisition of the reference image dataset the doctor determines within this three dimensional volume dataset one or multiple reference slices, that are especially significant for the doctor and of which the doctor requests subsequent exposures.

After the lapse of a time Δt, the current 3D image dataset is acquired as described in step b. In step c the registration of both 3D datasets subsequently occurs. This registration can be undertaken with any suitable registration technique. For example the gray scale value distribution of determined regions within the 3D image dataset can be used. After the registration, which both image datasets depict the same examination area, so the gray scale value distributions must be nearly the same, at least in the regions that have not changed pathologically, The control unit 3 then determines the gray scale value distribution of one or multiple registration slice(s) in the 3D reference image dataset. Subsequently a corresponding slice of specific gray scale value distribution is sought, which possesses the maximum concurrence with a corresponding registration slice gray scale value distribution in the 3D image dataset. A display instruction for registration of both datasets is ascertained when such a maximum concurrence is found. Besides the determination of a registration slice, it is naturally also possible to undertake the registration by means of a reference volume, FIG. 3 refers to a registration slice. The doctor working with a registration volume then would not define a registration slice (a two dimensional structure) but instead would designate a three dimensional volume in the reference image dataset. Again, a gray scale value distribution can form the basis for the registration.

The determination of the position of the slice for subsequent slice image acquisitions dependent upon the determined reference slice(s) follows in step d for the time at which the subsequent slice acquisitions are obtained. Again a comparison of the gray scale value distribution of the reference slice and the sought-for slice in the current 3D image dataset can be used.

Mapping of both slices with respect to one another is possible once a corresponding gray scale value distribution slice with the maximum concurrence with the distribution of the reference slice is found. Identification of the position of this slice in the present coordinate system then ensues, so the acquisition parameters can be ascertained and set as shown in step e.

Figure 4:
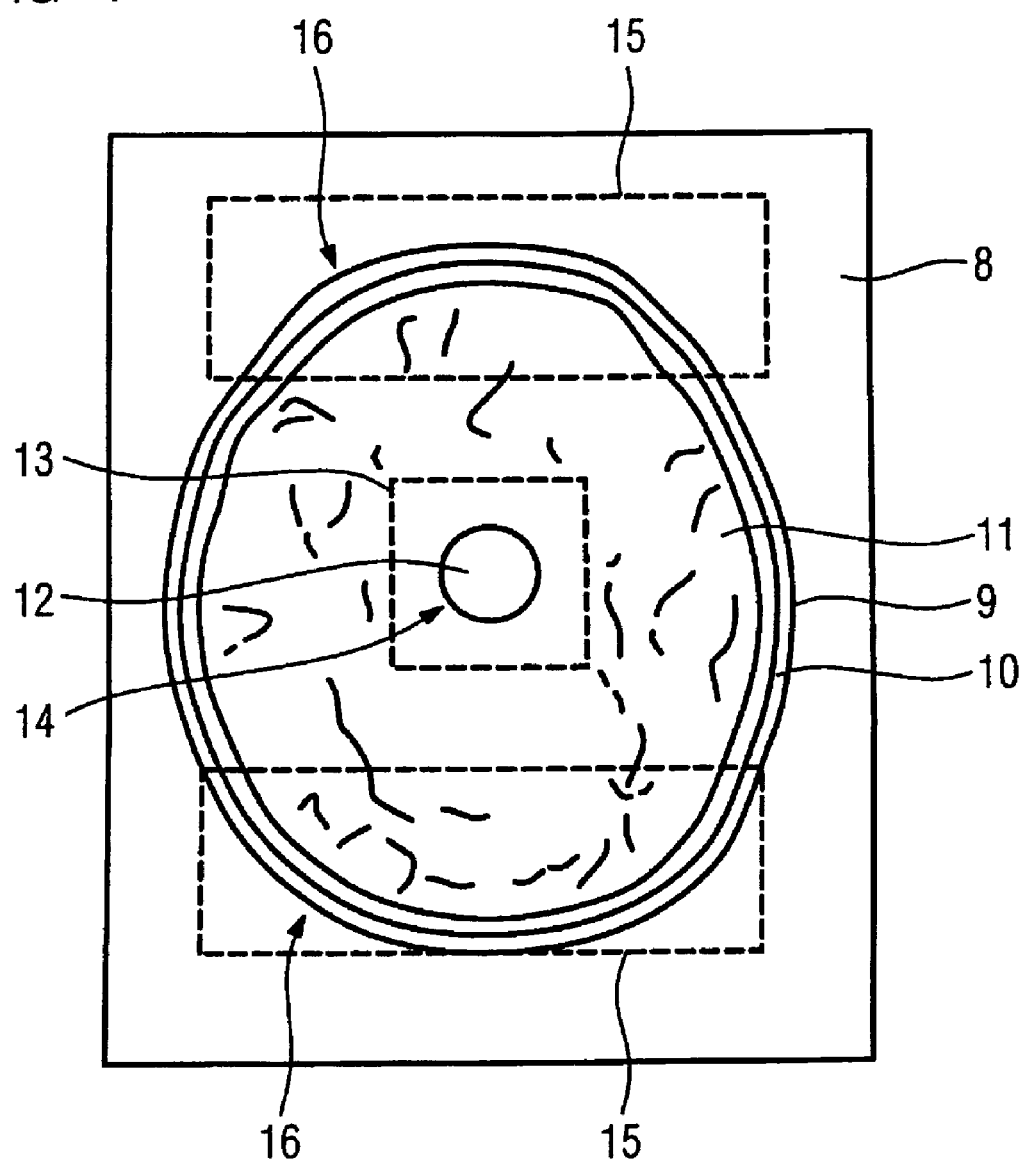
FIG. 4 illustrates a reference slice image with a depiction of different segmentation possibilities.

Since the reference slice proceeds through a pathological area in the examination region, as exactly this can be assessed within the framework of the subsequent examination, the possibility exists that the gray scale value distribution within this slice in the time Δt between two exposures will change due to a pathological change (for better or worse), For example the anatomy within a slice may change due to a shrinking or enlargement of a tumor, and so the gray scale value distribution changes as well. This means the concurrence of the gray scale value distribution between the reference slice image and the sought-after slice in such a case may not be high, so that it becomes difficult to find the right slice. To counteract this (as needed), one or multiple regions within the reference slice image can be segmented (one such segmented slice 8 is depicted in FIG. 4). The segmented areas can either be not at all considered at all in the gray scale value distribution, or can be considered exclusively.

FIG. 4 depicts a cross section of a head as a reference slice image 8, in which this example the cranial bone 10, the brain 11 as well as the tumor 12 (in the middle) are depicted. This tumor 12 shrinks upon successful treatment or grow in a failed treatment. In any case, a displacement of brain regions near to the tumor occurs, i.e. the anatomy changes, and consequently the gray scale value distribution in the cross-section changes as well. The doctor can now define, as shown via the shaded markings 13, a region 14 that exists around the tumor 12. This region 14 will not be considered in the framework of the gray scale value analysis for comparison of gray scale values. The regions of the brain existing outside of this area remain mostly unchanged during the change in size of the tumor 12, i.e. the anatomy in the outer regions of the head remain unchanged. Moreover, it is possible to create sufficiently stable gray scale value ratios.

An alternative is to mask out an image region by markings, such as the markings 15 to define a region 16 that will be considered exclusively in the gray scale value analysis for comparison of gray scale values. For this purpose the doctor chooses regions that remain unchanged despite a change of the tumor 12. Additionally or alternatively it is possible to define the respective slice section by means of anatomical markings. The cranial bone 10 is chosen for this purpose as an example, since it possesses a recognizable geometry and size in the reference slice (dependent upon the position in the slice). In the framework of the slice determination, using an appropriate image analysis algorithm, the geometry and size can be ascertained and used for the slice determination.

Just as it is possible in the slice selection determination to segment determined regions in the reference cross-section, it is also possible to define, for registration, registration slices in the 3D reference image dataset or registrations volumes, it is also possible, by segmentation of the dataset to produce preferential regions whose gray scale value distribution is considered either exclusively or remain are not considered at all in the registration procedure.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a medical imaging apparatus adapted to receive a patient therein, comprising the steps of:
   in a freely selectively acquired 3D reference image dataset of a patient, electronically designating a reference data slice;
   using a medical imaging apparatus, acquiring a 3D image dataset of an examination volume of a patient in the medical imaging device;
   automatically electronically bringing said 3D image dataset into registration with said 3D reference image dataset; and
   automatically electronically identifying a slice in said 3D image dataset, for which data are to be acquired in said medical imaging apparatus, corresponding to said reference data slice in the 3D reference image dataset that has been brought into registration with said 3D image dataset.

2. A method as claimed in claim 1 comprising acquiring said 3D reference image dataset with said patient in said medical imaging apparatus prior to acquiring said 3D image dataset.

3. A method as claimed in claim 1 comprising acquiring said 3D reference image dataset in a medical imaging apparatus other than said medical imaging apparatus in which said 3D image dataset is acquired, and entering said 3D reference image dataset into a control unit of said medical imaging apparatus in which said 3D dataset is acquired and bringing said 3D reference dataset and said 3D image dataset into registration, and identifying said slice in said 3D dataset, in said control unit.

4. A method as claimed in claim 1 comprising identifying said slice in said 3D image dataset by analyzing a gray scale value distribution of said 3D image dataset with respect to a gray scale value distribution of said reference data slice.

5. A method as claimed in claim 4 comprising identifying said slice in said 3D image dataset as a slice in said 3D image dataset that has a maximum concurrence of its gray scale value distribution with the gray scale value distribution of said reference slice.

6. A method as claimed in claim 1 comprising designating multiple reference data slices in said 3D reference image dataset and identifying multiple slices in said 3D image dataset respectively corresponding to said multiple reference data slices.

7. A method as claimed in claim 6 wherein each of said reference slices has a gray scale value distribution, and comprising identifying said multiple slices in said 3D image dataset as slices in said 3D image dataset respectively having a gray scale distribution exhibiting a maximum concurrence with the respective gray scale value distributions of said reference slices.

8. A method as claimed in claim 1 comprising segmenting said reference slice to designate a region therein that does not electronically contribute to the identification of the corresponding slice in the 3D image dataset.

9. A method as claimed in claim 1 comprising segmenting said reference data slice to designate a region therein that is exclusively used for the identification of said slice in said 3D image dataset corresponding to said reference slice.

10. A method as claimed in claim 1 comprising electronically marking an anatomical structure in said 3D reference image dataset and electronically designating said reference slice dependent on said anatomical structure.

11. A method as claimed in claim 1 comprising electronically marking an anatomical structure in said 3D reference image dataset and electronically bringing said 3D image dataset and said 3D reference image dataset into registration dependent on said anatomical structure.

12. A method as claimed in claim 1 comprising, after identifying said slice in said 3D image dataset, automatically setting operating parameters in a control unit of said medical imaging apparatus for acquiring data from the patient in said slice identified in said 3D image dataset.

13. A medical imaging apparatus comprising:

a control unit containing a freely selectively acquired 3D reference image dataset of a patient;

an interface connected to said control unit allowing designation of a reference data slice in said 3D reference image dataset;

a scanner adapted to receive the patient therein and operated by said control unit to acquire a 3D image dataset of an examination volume of the patient in the scanner;

said control unit automatically electronically bringing said 3D image dataset into registration with said 3D reference image dataset; and said control unit automatically electronically identifying a slice in said 3D image dataset, for which data are to be acquired in said medical imaging apparatus, corresponding to said reference data slice in the 3D reference image dataset that has been brought into registration with said 3D image dataset.

* * * * *